(12) United States Patent
Chung et al.

(10) Patent No.: US 9,980,736 B2
(45) Date of Patent: May 29, 2018

(54) DETACHABLE MEDICAL ELECTRIC TOOL

(71) Applicant: TECHWAY INDUSTRIAL CO., LTD., Taichung (TW)

(72) Inventors: Fu-Hsiang Chung, Taichung (TW); Chen-Chen Cheng, Taichung (TW); Jui-Heng Lin, Taichung (TW)

(73) Assignee: TECHWAY INDUSTRIAL CO., LTD., Taichung (TW)

( * ) Notice: Subject to any disclaimer, the term of this patent is extended or adjusted under 35 U.S.C. 154(b) by 206 days.

(21) Appl. No.: 14/994,680

(22) Filed: Jan. 13, 2016

(65) Prior Publication Data

US 2017/0196545 A1    Jul. 13, 2017

(51) Int. Cl.
*A61B 17/00* (2006.01)
*A61B 17/16* (2006.01)

(52) U.S. Cl.
CPC .. *A61B 17/1622* (2013.01); *A61B 2017/0046* (2013.01); *A61B 2017/00464* (2013.01); *A61B 2017/00477* (2013.01); *A61B 2017/00734* (2013.01)

(58) Field of Classification Search
CPC ....... A61B 17/00; A61B 17/141; A61B 17/16; A61B 17/1615; A61B 17/1659; A61B 2017/0046; A61B 2017/00464; A61B 2017/00477; A61B 2017/00734

USPC ............................................................ 606/1
See application file for complete search history.

(56) References Cited

U.S. PATENT DOCUMENTS 6,656,626 B1 * 12/2003 Mooty .................. B23D 51/01
                                                          30/500
7,414,211 B2 * 8/2008 Elsworthy ................. B25F 3/00
                                                          200/1 V

* cited by examiner

*Primary Examiner* — Aaron Roane
(74) *Attorney, Agent, or Firm* — Withrow & Terranova, P.L.L.C.; Vincent K. Gustafson

(57) ABSTRACT

A medical electric tool has a grip portion and a driving portion. The grip portion has a combining protrusion, two combining channels, and a locking device. The combining channels are defined respectively in two sides of the combining protrusion. The locking device is mounted in the combining protrusion and has two locking blocks and two recoil springs. Each locking block has an engaging segment. The engaging segment is formed on one end of the locking block and extends into one of the combining channels. The driving portion is detachably mounted on the combining protrusion on the grip portion and has a bottom face and two engaging ribs. Each engaging rib has an end provided with an engaging hook selectively engaging with the engaging segment of a corresponding one of the locking blocks.

2 Claims, 7 Drawing Sheets

DETACHABLE MEDICAL ELECTRIC TOOL

BACKGROUND OF THE DISCLOSURE

1. Field of the Disclosure

The present disclosure relates to an electric tool, and more particularly to a detachable medical electric tool.

2. Description of Related Art

In a medical process, such as performing an operation, multiple different electric tools, such as a saw, a drill, or a file may be needed. Therefore, multiple different electric tools have to be prepared for a medical process. A conventional electric tool substantially comprises a body and a tool portion. The body comprises a driving device and a switch and so on. The tool portion may be a saw blade, a drill head or a file blade, is connected to the body, and is driven by the driving device for different medical actions.

However, the medical electric tools have to be discarded after use to prevent cross infections or blood pollutions. In a next medical process, a new set of electric tools has to be prepared and used. Therefore, the cost for using the conventional medical electric tools is high, and the conventional medical electric tool is wasteful in use.

To overcome the shortcomings, the present disclosure tends to provide a medical electric tool to mitigate or obviate the aforementioned problems.

SUMMARY OF THE DISCLOSURE

The main objective of the disclosure is to provide a medical electric tool that is detachable to reduce the cost of using the medical electric tool and to prevent waste of resources in use.

The medical electric tool has a grip portion and a driving portion. The grip portion has a top face, a combining protrusion, two combining channels, two electrical sockets, and a locking device. The combining protrusion is formed on the top face and has two sides. The combining channels are defined respectively in the sides of the combining protrusion. The electrical sockets are mounted on the combining protrusion. The locking device is mounted in the combining protrusion and has two locking blocks and two recoil springs. The locking blocks are mounted in the combining protrusion, and each locking block has two ends, an engaging segment, and a pressed segment. The engaging segment is formed on one of the ends of the locking block and extends into one of the combining channels. The pressed segment is formed on the other end of the locking block and is exposed from the combining protrusion. The recoil springs are mounted in the combining protrusion and abut respectively on the pressed segments of the locking blocks to enable the engaging segment to extend into a corresponding one of the combining channels and the pressed segment to be exposed from the combining protrusion. The driving portion is detachably mounted on the combining protrusion on the grip portion and has a bottom face, two electrical plugs, and two engaging ribs. The electrical plugs are mounted on the bottom face and are selectively inserted respectively into the electrical sockets on the grip portion. The engaging ribs are formed on the bottom face respectively at positions adjacent to two sides of the bottom face and are held respectively in the combining channels. Each engaging rib has an end provided with an engaging hook selectively engaging with the engaging segment of a corresponding one of the locking blocks.

Other objects, advantages and novel features of the disclosure will become more apparent from the following detailed description when taken in conjunction with the accompanying drawings.

DETAILED DESCRIPTION OF PREFERRED EMBODIMENT

Figure 1:
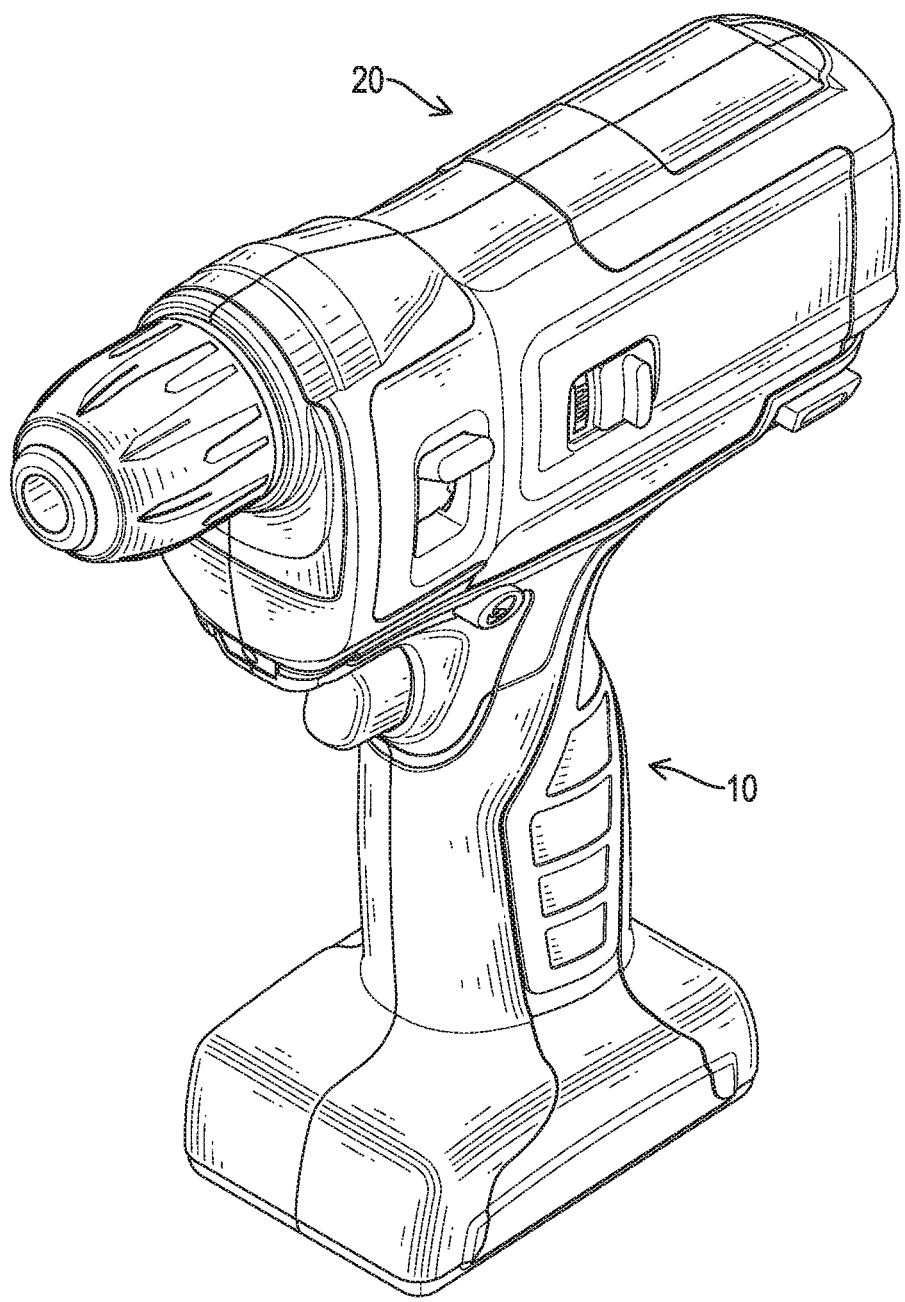
FIG. 1 is a perspective view of a medical electric tool in accordance with the present disclosure.
Figure 2:
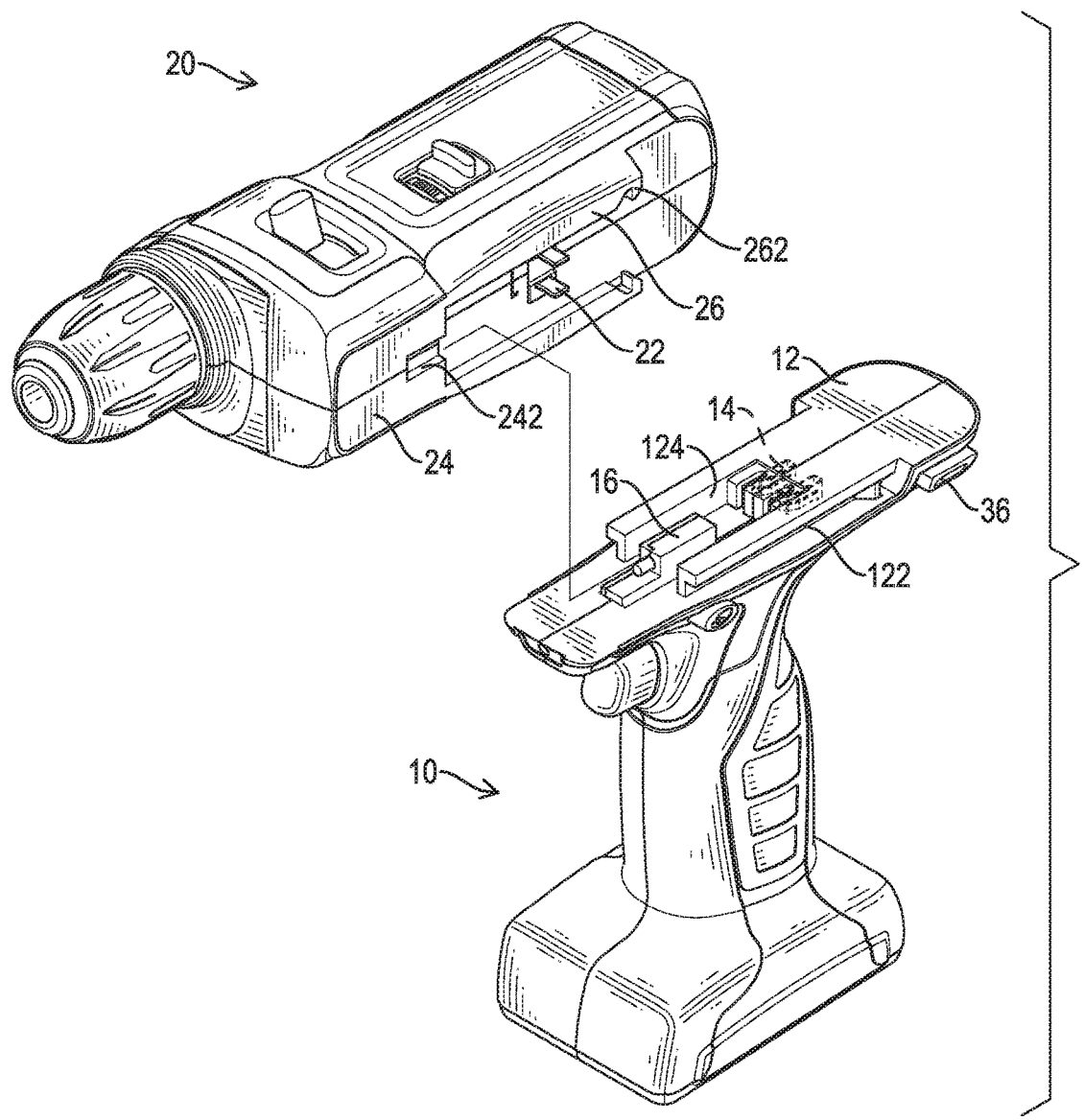
FIG. 2 is an exploded perspective view of the medical electric tool in FIG. 1.
Figure 3:
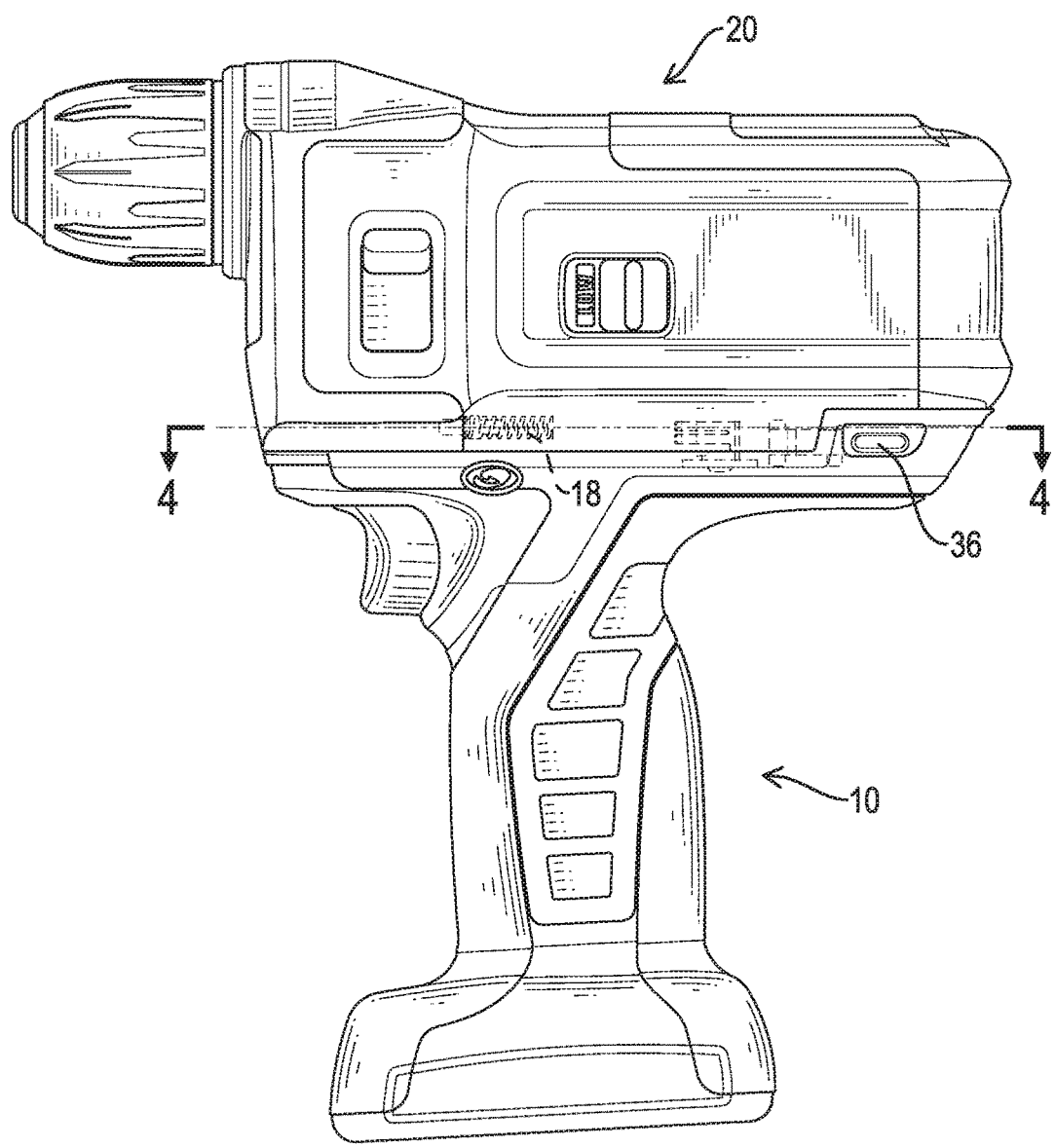
FIG. 3 is a side view of the medical electric tool in FIG. 1.
Figure 4:
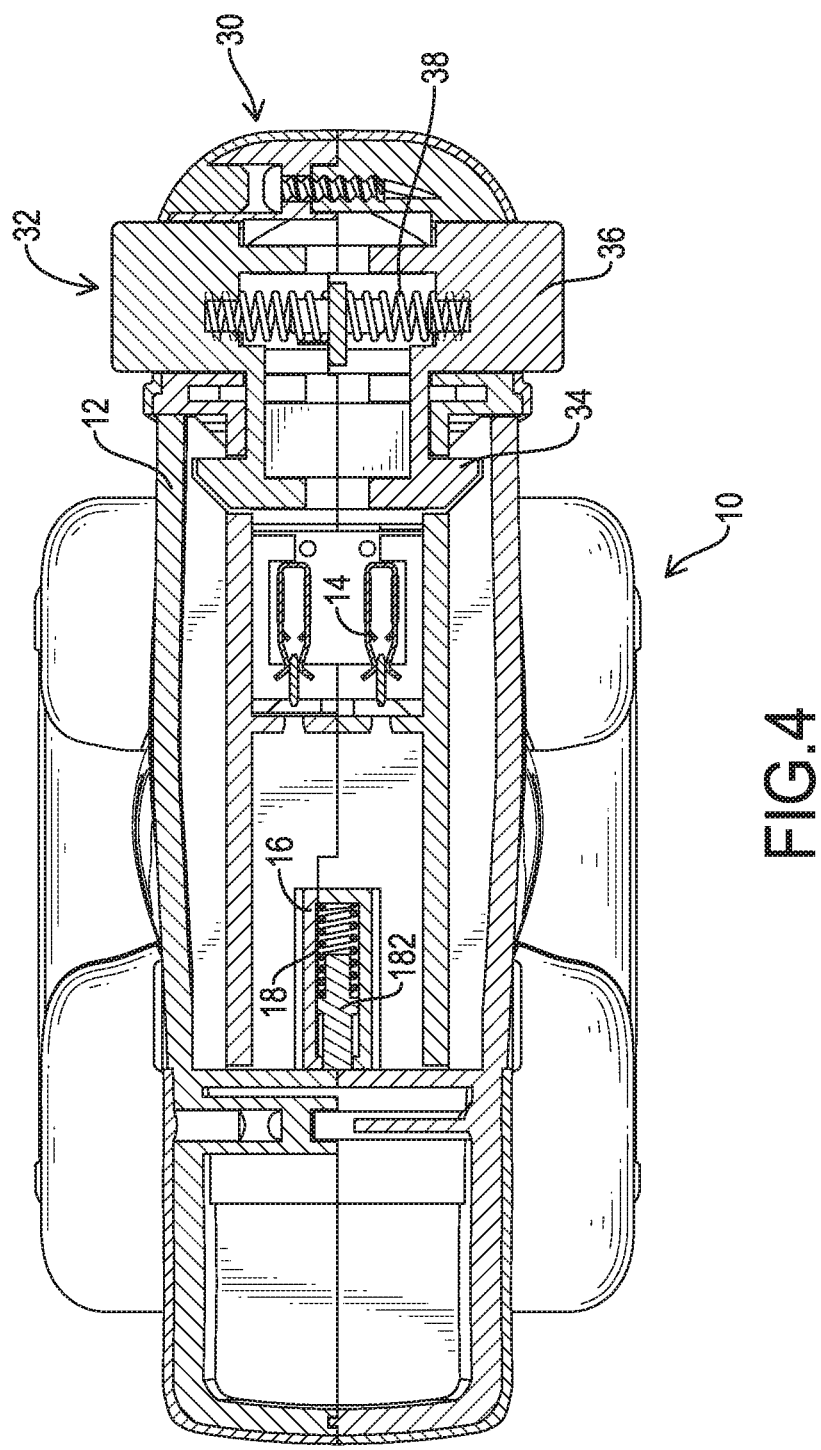
FIG. 4 is a top view in partial section of the medical electric tool along the line 4-4 in FIG. 3.
Figure 5:
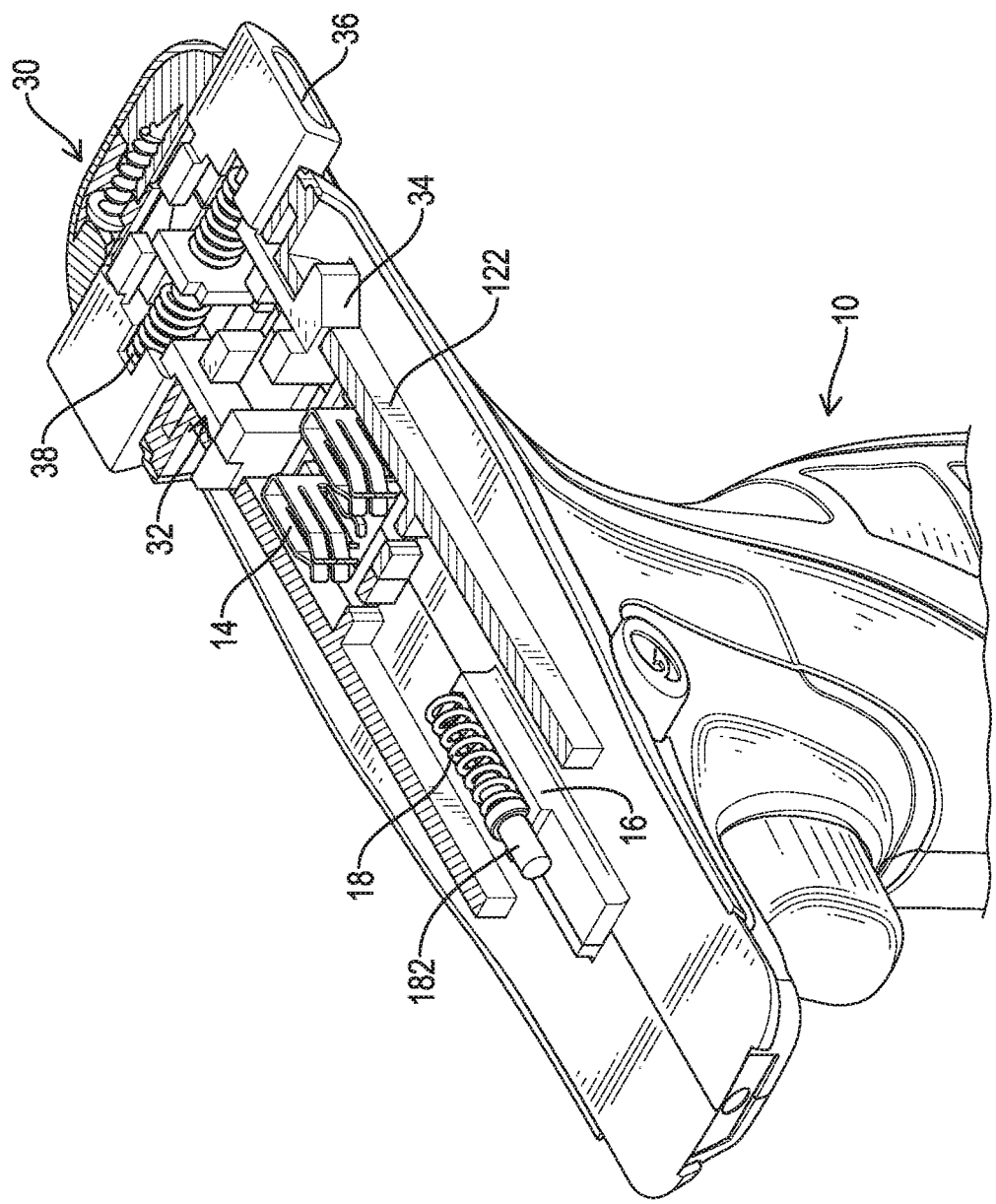
FIG. 5 is a perspective view in partial section of the grip portion of the medical electric tool in FIG. 1.

With reference to FIGS. 1 to 3, a medical electric tool in accordance with the present disclosure comprises a grip portion 10 and a driving portion 20. The grip portion 10 may have batteries, a power device and a switch mounted inside. The driving portion 20 may have a driving device, such as motor mounted inside. The power device, the switch, and the driving device in the grip portion 10 and the driving portion 20 may be conventional, and the detailed descriptions thereof are omitted.

With reference to FIGS. 2 to 5, the grip portion 10 has a top face, a combining protrusion 12, two combining channels 122, two electrical sockets 14, a locking device 30, a rod base 16, a resilient member 18, and a pushing rod 182. The combining protrusion 12 is formed on the top face of the grip portion 10 and has a top, two sides and a connection recess 124. The connection recess 124 is defined in the top of the combining protrusion 12. The combining channels 122 are defined respectively in the sides of the combining protrusion 12. The electrical sockets 14 are mounted on the combining protrusion 12 and are preferably mounted in the connection recess 124.

The locking device 30 is mounted in the combining protrusion 12 and comprises two locking blocks 32 and two recoil springs 38. The locking blocks 32 are mounted in the combining protrusion 12, and each locking block 32 has two ends, an engaging segment 34, and a pressed segment 36. The engaging segment 34 is formed on one of the two ends of the locking block 32 and extends into one of the combining channels 122. The pressed segment 36 is formed on the other end of the locking block 32 and is exposed from the combining protrusion 12. The recoil springs 38 are mounted in the combining protrusion 12 and abut respectively on the pressed segments 36 of the locking blocks 32 to enable the engaging segment 34 to extend into a corresponding one of the combining channels 122 and the pressed segment 36 to be exposed from the combining protrusion 12.

The rod base 16 is hollow, is formed on the top face of the grip portion 10, and is held in the connection recess 124. The resilient member 18 is mounted in the rod base 16 and may be a spring or a resilient block. The pushing rod 182 is mounted in the rod base 16 and has a first end abutting on the resilient member 18 and a second end extending out of the rod base 16.

The driving portion 20 is detachably mounted on the combining protrusion 12 on the grip portion 10 and comprises a bottom face, two electrical plugs 22, two engaging ribs 26, and a pushed block 24. The electrical plugs 22 are mounted on the bottom face and are selectively inserted respectively into the electrical sockets 14 on the grip portion 10. With the insertions of the electrical plugs 22 into the electrical sockets 14, the power device in the grip portion 10 and the driving device in the driving portion 20 are electrically connected with each other. The engaging ribs 26 are formed on the bottom face respectively at positions adjacent to two sides of the bottom face and are held respectively in the combining channels 122. Each engaging rib 26 has an end provided with an engaging hook 262 selectively engaging with the engaging segment 34 of a corresponding one of the locking blocks 32. The pushed block 24 is formed on the bottom face of the driving portion 20 and abuts on and is pushed by the pushing rod 182. In addition, the pushed block 24 further has a pushed recess 242 defined in the pushed block 24. The second end of the pushing rod 182 extends into the pushed recess 242 in the pushed block 24.

With such an arrangement, when the driving portion 20 is attached onto the top face of the grip portion 10, the ends having the engaging hooks 262 of the engaging ribs 26 are inserted respectively into the combining channels 122 and the engaging ribs 26 are slid along the combining channels 122. When the engaging ribs 26 are moved to a position where the engaging hooks 262 abut on the engaging segments 34 of the locking blocks 32, the engaging segments 34 of the locking blocks 32 will be pushed into the combining protrusion 12 and the recoil springs 38 are compressed. When the engaging hooks 262 pass over the engaging segments 34, the recoil springs 38 will push the engaging segments 34 into the combining channels 122 and engage respectively with the engaging hooks 262 on the engaging ribs 26. Accordingly, the driving portion 20 is securely combined with the grip portion 10 by the engagement between the engaging hooks 262 on the engaging ribs 26 and the engaging segments 34 of the locking blocks 32. At this time, the electrical plugs 22 are inserted respectively into the electrical sockets 14 to electrically connect the driving device with the power device. The pushed block 24 pushes against the pushing rod 182, and the resilient member 18 is compressed. A tool portion, such as a saw blade, a drill head or a file blade is connected with the driving portion 20. When the switch on the grip portion 10 is switched on, the tool portion is actuated to act for a corresponding medical action.

Figure 6:
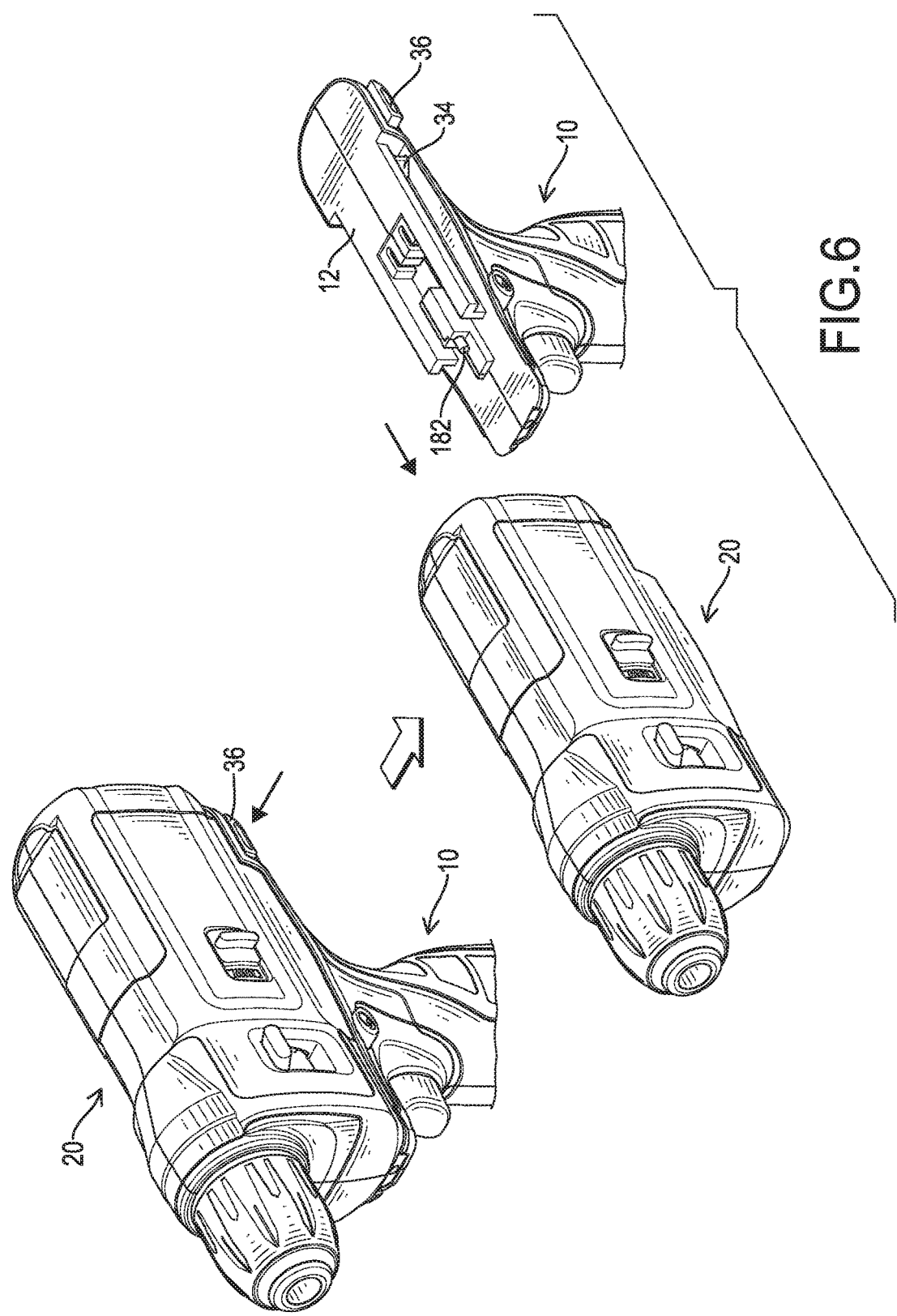
FIG. 6 shows operational perspective views of the medical electric tool in FIG. 1.
Figure 7:
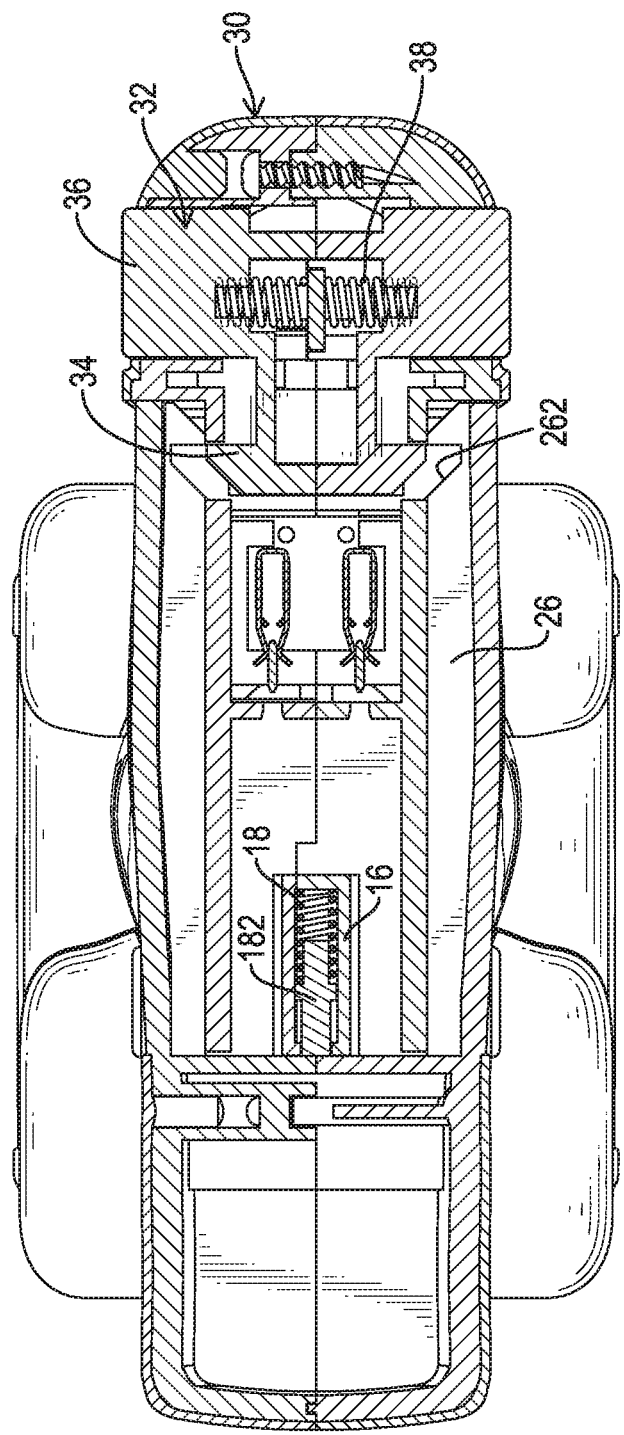
FIG. 7 is an operational top view in partial section of the medical electric tool in FIG. 1.

When the user wants to use different tools for different medical actions during a medical process, with reference to FIGS. 6 and 7, the pressed segments 36 of the locking blocks 32 are pressed into the combining protrusion 12. Consequently, the engaging segments 34 of the locking blocks 32 will be retracted into the combining protrusion 12 to disengage from the engaging hooks 262 on the engaging ribs 26, such that the driving portion 20 is unlocked from the grip portion 10. Accordingly, the compressed resilient member 18 will provide a force to the pushing rod 182 to push the pushed block 24 to move the driving portion 20 relative to the grip portion 10 in a forward direction. Thus, the driving portion 20 can be detached from the grip portion 10 along the forward direction, and another driving portion 20 with a different tool portion can be combined with the grip portion 10 for a next medical action. With the forward direction in which the driving portion 20 is pushed by the resilient member 18, the forward direction can provide the user with a guiding effect for detaching the driving portion 20 from the grip portion 10. Therefore, the medical electric tool can be easily detached.

With such an arrangement, only one single grip portion 10 is necessary and prepared for combining with different driving portions 20 with different tool portions during a medical process. During the medical process, a user can easily and conveniently change the driving portions 20 on the grip portion 10 for different medical actions. After the medical process is finished, although the used grip portion 10 and driving portions 20 have to be discarded, the cost of using medical electric tools is still reduced, and the waste of using the electrical tools can be prevented.

Even though numerous characteristics and advantages of the present disclosure have been set forth in the foregoing description, together with details of the structure and function of the disclosure, the disclosure is illustrative only, and changes may be made in detail, especially in matters of shape, size, and arrangement of parts within the principles of the disclosure to the full extent indicated by the broad general meaning of the terms in which the appended claims are expressed.

What is claimed is:

1. A medical electric tool comprising:
    a grip portion having
        a top face;
        a combining protrusion formed on the top face and having two sides;
        two combining channels defined respectively in the two sides of the combining protrusion;
        two electrical sockets mounted on the combining protrusion; and
        a locking device mounted in the combining protrusion and comprising
            two locking blocks mounted in the combining protrusion and each locking block having
                two ends;
                an engaging segment formed on one of the two ends of the locking block and extending into one of the combining channels; and
                a pressed segment formed on the other end of the locking block and exposed from the combining protrusion; and
            two recoil springs mounted in the combining protrusion and abutting respectively on the locking blocks to enable the engaging segment to extend into a corresponding one of the combining channels and the pressed segment to be exposed from the combining protrusion; and
    a driving portion detachably mounted on the combining protrusion on the grip portion and comprising
        a bottom face;
        two electrical plugs mounted on the bottom face and selectively inserted respectively into the electrical sockets on the grip portion; and
        two engaging ribs formed on the bottom face respectively at positions adjacent to two sides of the bottom face and held respectively in the combining channels, and each engaging rib having an end provided with an engaging hook selectively engaging with the engaging segment of a corresponding one of the locking blocks, wherein the combining protrusion further has a connection recess defined in a top of the combining protrusion;

the electrical sockets are mounted in the connection recess;

the grip portion further comprises
- a rod base being hollow, formed on the top face of the grip portion, and held in the connection recess;
- a resilient member mounted in the rod base; and
- a pushing rod mounted in the rod base and having a first end abutting on the resilient member and a second end extending out of the rod base; and the driving portion further has a pushed block formed on the bottom face of the driving portion and abutting on and pushed by the pushing rod.

2. The medical electric tool as claimed in claim 1, wherein the pushed block further has a pushed recess defined in the pushed block; and the second end of the pushing rod extends into the pushed recess in the pushed block.

\* \* \* \* \*